United States Patent
Boday et al.

(10) Patent No.: US 8,735,852 B2
(45) Date of Patent: May 27, 2014

(54) MATRIX-INCORPORATED FLUORESCENT SILICA FOR ANTI-COUNTERFEITING

(75) Inventors: Dylan J. Boday, Tucson, AZ (US); Jason T. Wertz, Wappingers Falls, NY (US)

(73) Assignee: International Business Machines Corporation, Armonk, NY (US)

( * ) Notice: Subject to any disclaimer, the term of this patent is extended or adjusted under 35 U.S.C. 154(b) by 94 days.

(21) Appl. No.: 13/447,416

(22) Filed: Apr. 16, 2012

(65) Prior Publication Data

US 2013/0270457 A1 Oct. 17, 2013

(51) Int. Cl.
*G01N 21/64* (2006.01)

(52) U.S. Cl.
CPC ..................................... *G01N 21/64* (2013.01)
USPC ..................................................... 250/459.1

(58) Field of Classification Search
CPC .............. G01N 21/64; G01N 21/6428; G01N 2021/6441; C07F 7/02
USPC ..................................................... 250/459.1
See application file for complete search history.

(56) References Cited

U.S. PATENT DOCUMENTS

| | | | |
|---|---|---|---|
| 7,394,997 B2 | 7/2008 | Mei et al. | |
| 7,682,523 B2 | 3/2010 | Weisman et al. | |
| 7,777,176 B2 | 8/2010 | Loy et al. | |
| 2005/0008858 A1 | 1/2005 | Wakefield et al. | |
| 2005/0019556 A1 | 1/2005 | Freeman et al. | |
| 2006/0148104 A1* | 7/2006 | Marini et al. | 436/524 |
| 2008/0182056 A1* | 7/2008 | Bakker et al. | 428/36.8 |
| 2010/0003204 A1 | 1/2010 | Loy et al. | |
| 2010/0062194 A1 | 3/2010 | Sun | |
| 2011/0008606 A1 | 1/2011 | Sun | |
| 2013/0084643 A1* | 4/2013 | Commarieu et al. | 436/27 |

FOREIGN PATENT DOCUMENTS

| | | |
|---|---|---|
| JP | 09-078013 A | 3/1997 |
| JP | 09-249834 A | 9/1997 |
| JP | 2008-003679 A | 1/2008 |
| WO | 2009140266 A2 | 11/2009 |

OTHER PUBLICATIONS

Canton et al., "Modified Stober synthesis of highly luminescent dye-doped silica nanoparticles," May 1, 2011, Journal of Nanoparticle Research, 8 pages.*

Auger et al., "A comparative study of non-covalent encapsulation methods for organic dyes into silica nanoparticles", Nanoscale Research Letters 2011 6:328, (Received Sep. 13, 2011/Accepted Apr. 13, 2011), Published online Apr. 13, 2011, Copyright © 2011 Auger et al; licensee Springer. DOI: 10.1186/1556-276X-6-328.

Bagwe et al., "Surface Modification of silica nanoparticles to reduce aggregation and non-specific binding", NIH Public Access Author Manuscript, NIHMS ID: NIHMS60976, pp. 1-13, (Published in final edited form as: Langmuir, Apr. 25, 2006; 22(9): 4357-4362). DOI: 10.1021/Ia052797j.

(Continued)

*Primary Examiner* — Kiho Kim
(74) *Attorney, Agent, or Firm* — Richard A. Wilhelm; Robert R. Williams

(57) ABSTRACT

The present invention relates to a fluorescent dye-incorporated silica material. A fluorescent dye is covalently bonded to a silica matrix. The invention also provides for a method for verifying the authenticity of a product, wherein the fluorescent silica material is present in or on a product, and the material is tested for fluorescence or structure.

18 Claims, 5 Drawing Sheets

(56) References Cited

OTHER PUBLICATIONS

Canton et al., "Modified Stober synthesis of highly luminescent dye-doped silica nanoparticles", Journal of Nanoparticle Research, Research Paper, (Received Oct. 18, 2010/Accepted Apr. 18, 2011), Published online May 1, 2011, Copyright Springer Science + Business Media B.V. 2011, Netherlands. DOI: 10.1007s11051-011-0382-3.

Hendrick et al., "Cellulose Acetate Fibers with Fluorescing Nanoparticles for Anti-counterfeiting and pH-sensing Applications", Journal of Engineered Fibers and Fabrics, 2010, pp. 21-30, vol. 5, issue 1, Published by INDA, Association of Nonwovens Fabrics Industry, USA.

* cited by examiner 4,4'-bis(4-(triethoxysilyl)styryl)biphenyl

*N,N'*-bis(3-triethoxysilylpropyl)-perylene-3,4:9,10-tetracarboxydiimide

MATRIX-INCORPORATED FLUORESCENT SILICA FOR ANTI-COUNTERFEITING

TECHNICAL FIELD

This disclosure is generally directed to fluorescent dye-incorporated silica, and methods for producing and using fluorescent dye-incorporated silica. One such usage may be for the verification of the authenticity of a product or the purchasing of such product.

BACKGROUND

Silica consists of silicon and oxygen. Due to the silicon's tetrahedral structure and upon reaction with oxygen, silica matrices can be formed. Silica matrices may form amorphous structures, such as mesoporous silica, which are unordered structures. A silica matrix can be used to form silica particles and silica films. During the formation of silica, the siloxane network can grow to a size which causes phase separation as silica particles. A silica matrix can be formed onto other surfaces as a coating. These silica particles and coatings have many applications in many fields, including agriculture, industry, and medicine.

SUMMARY

In one embodiment, the present disclosure provides a fluorescent material, comprising a silica matrix and first fluorescent dye compounds covalently bonded to the silica matrix, the first fluorescent dye compounds having a first emission wavelength.

In another embodiment, the present disclosure provides a method for producing a fluorescent material, comprising combining silane monomers and fluorescent silane dyes and initiating a polymerization reaction between the silane monomers and the fluorescent silane dye, thereby creating fluorescent dye compounds covalently bonded to a silica matrix.

In another embodiment, the present disclosure provides a method for verifying a genuine product, comprising exposing a fluorescent material to incident radiation, the fluorescent material comprising a silica matrix and first fluorescent dye compounds covalently bonded to the silica matrix, the first fluorescent dye compounds having a first emission wavelength and detecting emissive radiation having the first emission wavelength, to verify the authenticity of the product.

In another embodiment, the present disclosure provides a fluorescent material comprising a silica matrix, comprising silicon, oxygen, and first fluorescent dye compounds, wherein first fluorescent dye compounds are covalently bonded to at least some silicon atoms in the silica matrix.

BRIEF DESCRIPTION OF THE DRAWINGS

The drawings illustrate embodiments of the present invention and, along with the description, serve to explain the principles of the invention. The drawings are only illustrative of typical embodiments of the invention and do not limit the invention.

DETAILED DESCRIPTION

Figure 1:
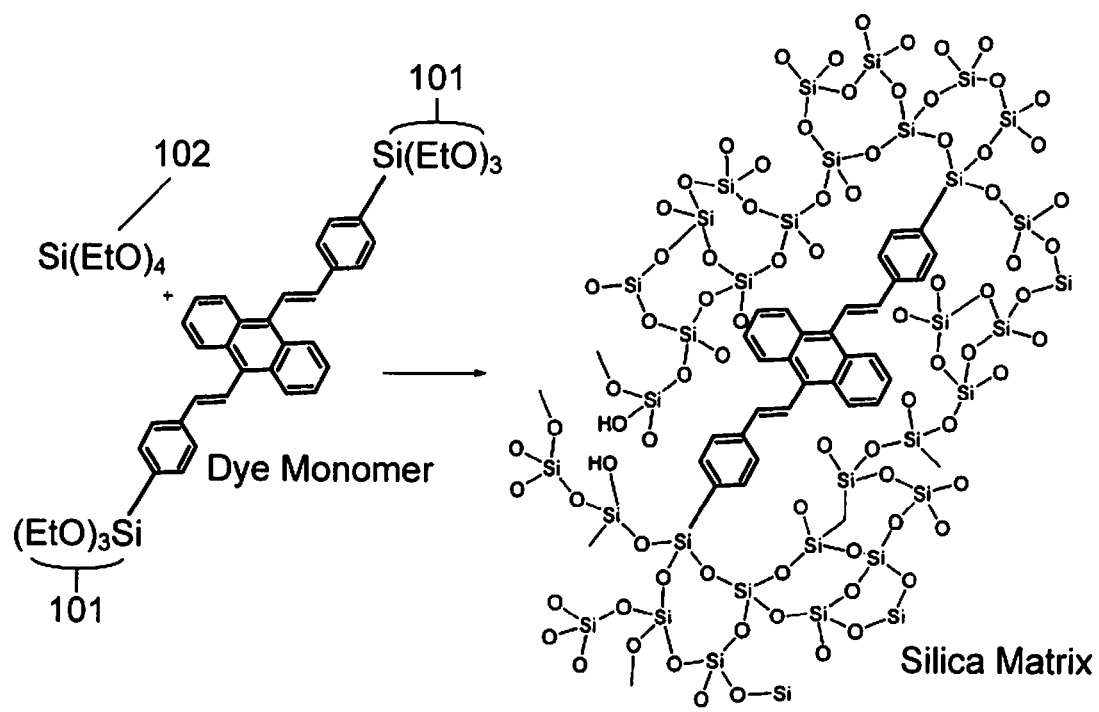
FIG. 1 depicts polymerization of a silane dye monomer and silane monomers to form a silica matrix, according to an embodiment of the invention.

The present invention relates to a fluorescent material containing a fluorescent dye incorporated into a silica matrix through covalent bonds. This structural incorporation of the dye into the matrix may aid in preventing the dye from leaching out of a material and may be achieved in a single step. Leaching is a phenomenon involving the washing out of an encapsulated substance by physical or chemical processes, such as diffusion. It may occur during formation, use, or storage of an encapsulated substance. Leaching may reduce the effectiveness of a substance, as the amount of the effective substance decreases. In the context of encapsulated fluorescent dyes, leaching may decrease the intensity or durability of the encapsulated dye. For applications such as product verification, this may have significant consequences.

According to principles of the invention, a substance containing a fluorescent material, such as paint, ink, or other physical substance, may provide for two levels of security for determining product authenticity. At a first level of security, the substance may contain a fluorescent material with a fluorescent dye integrated into a silica matrix of the fluorescent material, the fluorescent dye having an emission wavelength. Two or more fluorescent dyes may be integrated into the silica matrix, each of the dyes fluorescing at the same or a different wavelength. Additionally, two or more fluorescent materials with fluorescent dyes having different emission wavelengths may be added to the substance. By selecting fluorescent dyes with different emission wavelengths, goods marked or imbued with the fluorescent material may be uniquely tagged. The emission wavelengths of fluorescent dyes may cover a large range of wavelengths, and while addition of different fluorescent dyes is possible for the fluorescent material's manufacturer, detection of those different fluorescent dyes may be difficult for counterfeiters. See FIG. 4 for a visual representation of fluorescent material that does not fluoresce when exposed to household light, but fluoresces under two different wavelengths of radiation.

At a second level of security, structural characteristics or features of the fluorescent material may be used for identification. Silica particles or silica layers formed from the fluorescent material may be controlled for size and structure on a nanoscale. Observation of the size and structure of the fluorescent material on a nanoscale may require an electron microscope or similar apparatus. Such equipment may be prohibitively expensive for most counterfeiters, and this expense acts as an obstacle to making counterfeit goods. These two security levels together may form a two-tiered system of protection, which may be tailored to the quality, value, or other characteristic of an item. See FIG. 4 for a visual representation of structural examination of a fluorescent material utilizing electron microscopy, according to an embodiment of the invention.

Material Structure

In an aspect of the invention, a fluorescent material includes a silica matrix. This silica matrix may be polymerized from silane monomers, which form a network through covalent siloxane bonds. During material formation, a fluorescent silane dye may form siloxane bonds with the silane monomers and integrate into the silica matrix to form a fluorescent material. The resulting silica matrix will include silicon and oxygen forming siloxane bonds, as well as fluorescent dyes covalently bonded to silicon atoms. Due to this integration, a leach-resistant dye may be produced without an additional polymer shell, and the particle may be produced in one step. After material formation, the surfaces of the fluorescent material retain hydroxyl functional groups generated from incomplete condensation of the silica matrix. This surface may then be modified to change the fluorescent material's dispersion properties. The surface may be further modified with additional fluorescent dyes, functionalities to target specific regions within biological systems, and other functionalities to aid in application where a fluorescent core may be used. The size of the fluorescent material may be controlled for homogeneity. Fluorescent silane dyes that may be used include, but are not limited to, fluorescent vinyl silane dyes and fluorescent pyrene silane dyes.

Figure 2:
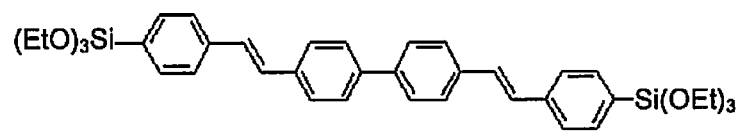
FIG. 2 depicts two bridged fluorescent silane dyes that may be integrated into a silica matrix, according to an embodiment of the invention.
Figure 2:
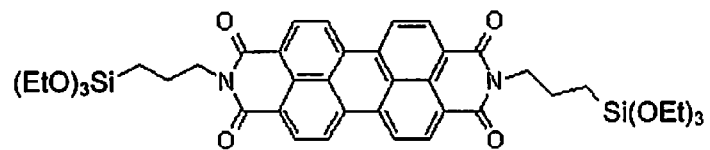

In an aspect of the invention, a bridged fluorescent silane dye may be used to form a silica matrix with silane monomers. The bridged fluorescent silane dye may have up to six sites—three on each of the two silicon atoms—for covalently bonding into the structure of the silica matrix, as seen in FIG. 1. As mentioned above, these covalent bonds may help prevent leaching of the dye. The bridged fluorescent silane dye may have an emission wavelength anywhere on the electromagnetic spectrum, depending on the desired fluorescent properties of the dye. Bridged fluorescent silane dyes that may be used include, but are not limited to, 4,4'-bis(4-(triethoxysilyl)styryl)biphenyl and N,N'-bis(3-triethoxysilylpropyl)-perylene-3,4:9-10-tetracarboxdiimide. FIG. 2 depicts these two bridged fluorescent silane dyes, according to aspects of the invention.

FIG. 1 depicts incorporation of a bridged fluorescent silane dye into a silica matrix, according to aspects of the invention. A dye monomer has two silane sites 101. One or both silane sites 101 form siloxane bonds with a silica monomer 102, in this case tetraethyl orthosilicate, to form a silica matrix, where the dye is part of the matrix.

According to embodiments of the invention, the fluorescent material may form fluorescent silica particles or fluorescent silica layers. Silanol functionalities retained on the surface of the fluorescent material may be used for further modification, and the fluorescent material's properties may be changed in order to better disperse it in aqueous or organic dispersions or to reduce agglomeration. Functional groups on the surface of the fluorescent material may change the polarity of the material's surface, or decrease the van der Waals interactions between particles of the material, which may increase material dispersion and decrease material agglomeration. In an aspect of the invention, a surface of the fluorescent material contains a functional group that increases the dispersion of the material in a particular medium or decreases agglomeration of the particles. For example, a functional group may be selected for its hydrophobic properties, such as a phenyl group, for dispersion in organic or oil-based dispersions. The functional group used for surface modification may differ with the properties of the substance in which it is dispersed. Such functional groups may include, but are not limited to, polyethylene glycol, carboxyl, amino, methyl, and benzyl.

Material Formation

In an aspect of the invention, a fluorescent material may be formed by polymerization of silane monomers. These silane monomers undergo hydrolysis and condensation reactions to form covalent bonds, forming a silica matrix. These silane compounds include fluorescent silane dyes, which have one or more bonding sites to form siloxane bonds.

In an embodiment, fluorescent silica nanoparticles may be formed using the Stöber process, which may create monodisperse silica particles. In the Stöber process, alkoxysilane compounds, such as tetraethyl orthosilicate (TEOS), are mixed with a water, ammonia, and alcohol solution to form an alkoxysilane solution. Alkoxysilane compounds undergo hydrolysis, forming silanol compounds and alcohols. Alkoxysilane compounds may undergo both alcohol condensation, in which an alkoxysilane compound reacts with a silanol compound, and water condensation, in which a silanol compound reacts with another silanol compound. These condensation reactions produce a silica matrix. The above described reactions may be as follows:

Hydrolysis

Condensation-Alcohol

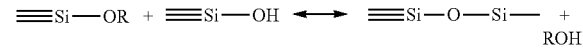

Condensation-Water

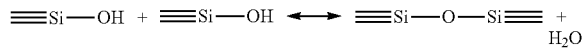

Overall

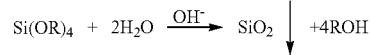

where R may be an alkyl group. The size of the silica particles formed by this process may be controlled through changing the amount of water or ammonia used in the process. Any alkoxysilane compound may be used as a silica monomer in material formation including, but not limited to, tetraethyl orthosilicate (TEOS) and tetramethyl orthosilicate (TMOS).

Figure 3:
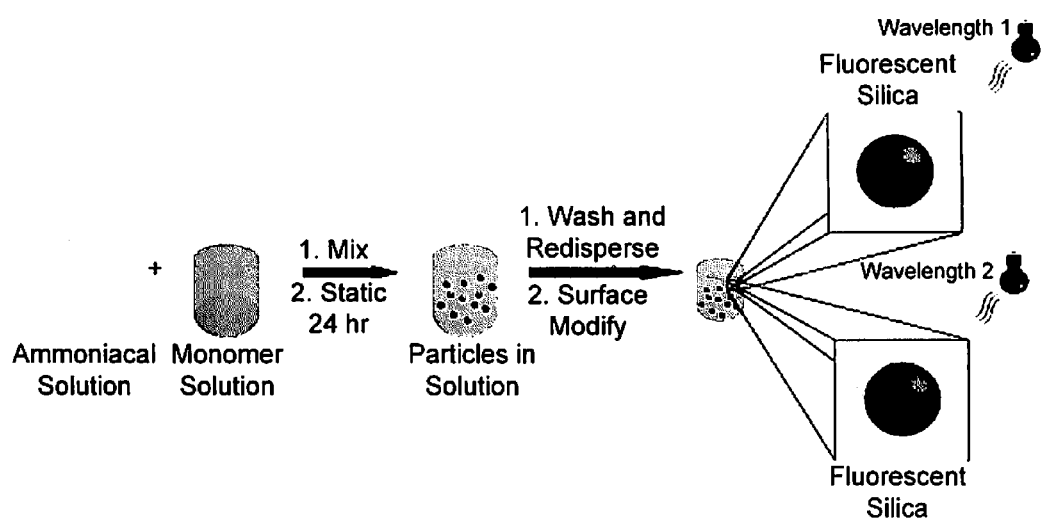
FIG. 3 depicts a method for producing fluorescent dye-incorporated silica particles, according to an embodiment of the invention.

The Stöber process may be modified to covalently incorporate a fluorescent dye into the silica matrix by adding one or more fluorescent silane dyes to the initial alkoxysilane solution. These fluorescent silane dyes may undergo hydrolysis by the same mechanism as an alkoxysilane compound, and form up to three siloxane bonds with the silica matrix on each of its trialkoxysilyl groups, for a total of up to six bonds. FIG. 3 depicts formation of fluorescent silica particles using a modified Stöber process, according to an embodiment of the invention.

In another embodiment, the fluorescent material may be formed using a microemulsion process. A microemulsion process may contain the same hydrolysis and condensation steps as those of the Stöber process documented above, but the environment for polymerization may be different. In one embodiment of the invention, a surfactant is mixed with a water and ammonia solution to form an aqueous phase. Alkoxysilane monomers and bridged fluorescent silane dyes are dispersed into the aqueous phase, forming micelles with the surfactant in the aqueous phase. A polymerization reaction is initiated between silane monomers and silane dyes within the micelles, forming a silica matrix. Any surfactant may be used, including but not limited to non-ionic polyoxyethylene nonylphenyl ether, polyethylene glycol alkyl ether, and sodium dodecyl sulfate. If desired, an oil solvent may be added to the aqueous phase to form part of the micelles with the silane compounds. Oil solvents that may be used include, but are not limited to, toluene, cyclohexane, and heptane.

In an embodiment of the invention, the fluorescent material may have a dispersive functional group on its surface. The dispersive functional group may be attached to a silanol group on the fluorescent material's surface to increase dispersion of the fluorescent material in different media, such as paints and oils, or decrease agglomeration of the fluorescent material. In an embodiment, the fluorescent material is treated with a dispersive functional group, such as a hydrophilic polyethylene glycol. For example, a silane agent may be used to attach the polyethylene glycol to hydroxyl groups on the surface of a silica particle, as described in the experimental section below.

Product Verification and Anti-Counterfeit Security

According to the principles of the invention, a substance containing a fluorescent material may be an ink, paint, or other physical substance used to coat all or a portion of a surface of any product. In addition, fluorescent silica material, according to the principles of the invention, may be a part of the substance used to make all or part of any product. For example, a product may include a part made from a substance that includes fluorescent material dispersed in that substance. Moreover, the material may be used in or on packaging for or a tag attached to any product.

A "product" may be any suitable product. Further, a product may be any packaging surrounding or attached to a product. A product may be any product used by business, government, or consumers. Examples of products include any integrated circuit and any circuit board having parts formed from or painted with a substance having a fluorescent material, according to the principles of the invention. Other examples include consumer products, such as handbags, clothing, shoes, watches, jewelry, and electronic devices, such as cellular telephones having any part formed from a substance containing a fluorescent material, according to the principles of the invention, or having a portion of a surface coated or painted with a substance containing a fluorescent material, according to the principles of the invention. In one embodiment, a "product" may be a tag attached to a consumer product, such as an article of clothing, wherein the tag may be formed from or painted with a substance having a fluorescent material, according to the principles of the invention. An additional example of a product having a substance formed from a fluorescent material, according to the principles of the invention, may be packaging for any pharmaceutical product. For example, pharmaceuticals are commonly packaged in plastic bottles with labels affixed to the bottles. The plastic from which a bottle is made may include fluorescent material as described herein or a label affixed to the bottle may have an ink printed thereon that includes fluorescent material as described herein. As an additional example, a pharmaceutical product, such as a tablet or a capsule, may include a material having fluorescent material as described herein.

Figure 4:
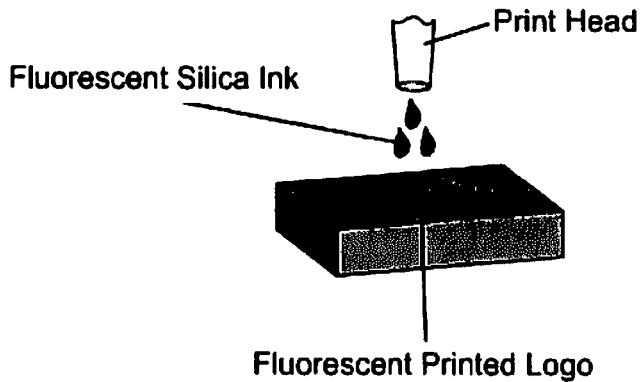
FIG. 4 depicts a use for fluorescent dye-incorporated silica particles, according to an embodiment of the invention.
Figure 4:
Figure 4:
Figure 4:
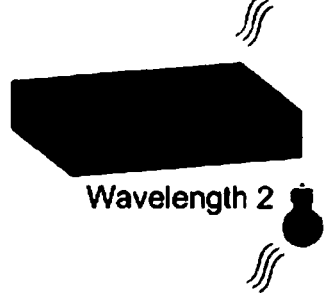
Figure 4:
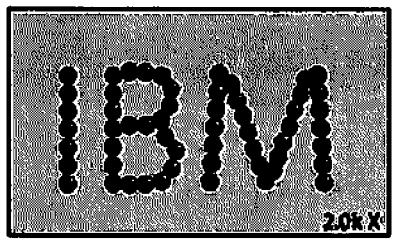

In one embodiment, a fluorescent material may have one type of fluorescent dye integrated into a silica matrix, which may be referred to as a first fluorescent dye. The first fluorescent dye may have an emission wavelength in or above the visible spectrum. For example, in one embodiment, the first fluorescent dye may have an emission wavelength of greater than 750 nm. As another example, the first fluorescent dye may have an emission wavelength of greater than 390 nm. In an alternative embodiment, a fluorescent material may have two or more fluorescent dyes integrated into a silica matrix. For example, a first fluorescent dye may have an excitation wavelength around 365 nm and an emission wavelength around 400 nm, while a second dye may have an excitation wavelength around 765 nm and an emission wavelength around 800 nm. In this example, the silica particles may be surface modified with a polarizing functional group and dispersed into a polar application system, such as an aqueous paint. The paint may be applied to a product. In one embodiment, the product may be irradiated with radiation at a wavelength of 365 nm to check for fluorescence at 400 nm. In an alternative embodiment, the product may be irradiated with radiation having a wavelength of 365 nm to check for fluorescence at 400 nm, and may be irradiated with radiation having a wavelength of 765 nm to check for fluorescence at 800 nm. If fluorescence is detected at both emission wavelengths, then the product may be verified as authentic. If fluorescence isn't present at both wavelengths, the product may be identified as counterfeit. A counterfeiter must know to check a product for fluorescence, and must also know to check at multiple wavelengths. FIG. 4 depicts an application for fluorescence of silica particles for use in logos.

In one embodiment, the fluorescent material may be present in a substance in a concentration sufficient to affect the intensity of the substance's fluorescence. In one embodiment of the invention, the concentration of the fluorescent material dispersed in a substance may be varied to change the intensity of the fluorescence, as an additional security check for counterfeiting. The fluorescent material may be present in any concentration sufficient to allow the material to fluoresce at a desired intensity for an application. In one embodiment, a material may fluoresce at an intensity that may generally be observed without the aid of any equipment or machine. In an alternative embodiment, the material may fluoresce at an intensity that may generally be observed with the aid of equipment or a machine. In another alternative embodiment, a material may fluoresce at an emission wavelength above the visible spectrum, requiring the use of equipment or a machine to detect fluorescence.

In another embodiment, the authenticity of a product may be determined by examining nanoscale features of a substance in or on the product using alternative microscopic techniques, such as electron microscopy. Silica particles, according to the principles of the invention, may be applied to a product as an ink, paint, or coating. Moreover, the substance from which any part of the product is made may include the fluorescent material, according to the principles of the invention. The region of the product where the material containing silica particles is painted or coated may be examined with an electron microscope. Similarly, a part of the product that is made from a substance that includes the fluorescent material may be examined with an electron microscope. The use of an electron microscope allows a structural characteristic such as the size or shape of the silica particles, formed from the fluorescent material, to be examined. For example, the process of forming silica particles may be controlled in order to create silica particles of a certain homogeneous size or shape, such as through changing the concentration of products or reactants during the reaction. To test for product authenticity, the size or shape of silica particles in a material may be inspected and compared with the "controlled for" size or shape of the silica particles. For particularly expensive or unique products, a counterfeiter may determine the proper emission wavelengths for the fluorescent dyes, and apply them to the counterfeit product, but might not properly determine the size or physical structure of the silica particles. The inspection of silica particle shape or size using electron microscopy may be in addition to or as alternative to other embodiments described in this description, e.g., the integration of fluorescent dyes. FIG. 4 depicts an application for electron microscopy of silica particles for use in determining the authenticity an insignia or logo, according to an embodiment of the invention.

These different levels of security may be tailored to an anti-counterfeit system according to the needs of the business and characteristics of the product. For selected items, based on the items' cost, importance, or other distinguishing factor, a system may be tailored to test for fluorescence at multiple wavelengths. But for more expensive or unique items, the electron microscope may be applied. The actual anti-counterfeiting medium need not change, only the systems used to check for counterfeiting, though characteristics of the material such as dilution may be changed to allow for customization.

Figure 5:
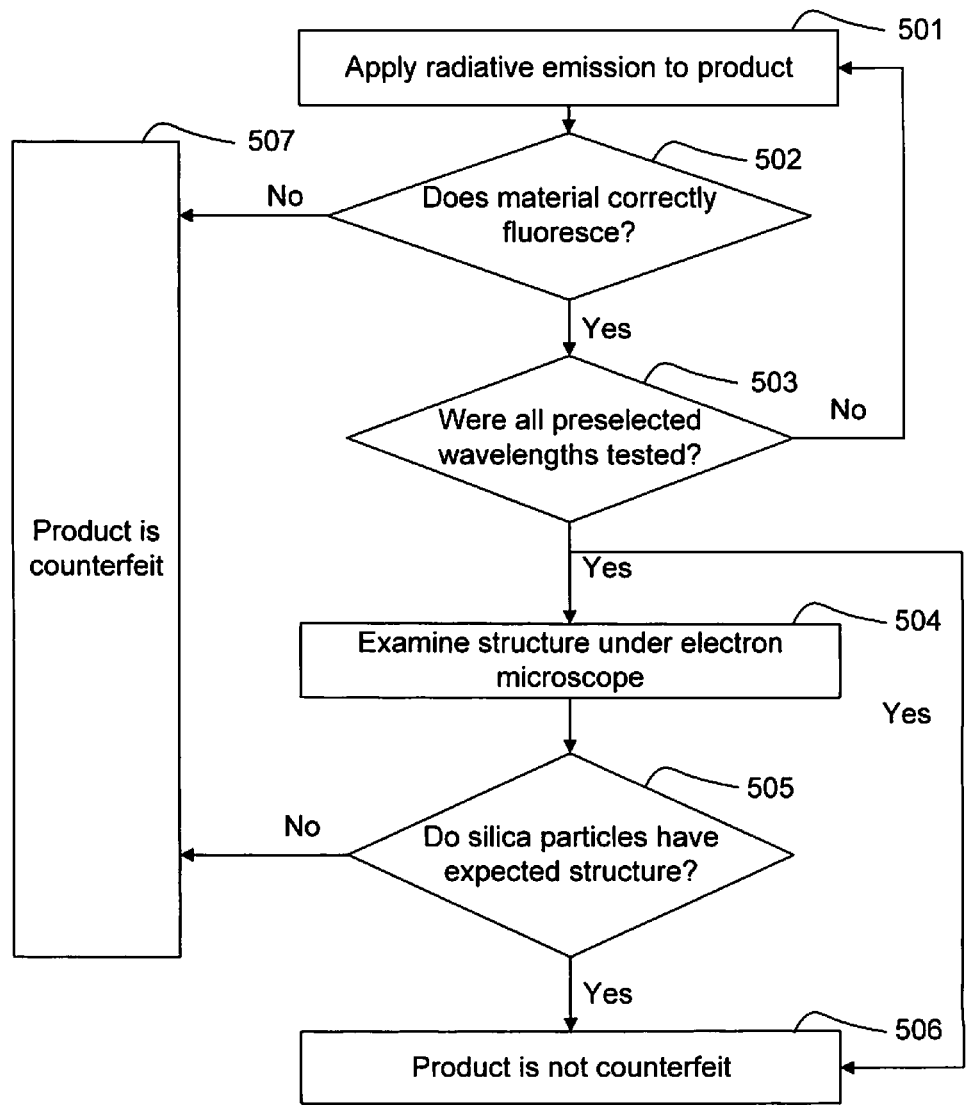
FIG. 5 depicts methods for using fluorescent dye-incorporated silica to verify product authenticity, according to embodiments of the invention.

FIG. 5 depicts an exemplary method for determining whether a product is authentic according to embodiments of the invention. In 501, a product having a fluorescent material, according to the principles of the invention, is exposed to incident radiation of a predetermined excitation wavelength. In one embodiment, all or part of the material is exposed to incident radiation. In 502, fluorescence may be checked at a first predetermined emission wavelength; if the material does not fluoresce at the correct wavelength, then it may be determined that the product is not authentic, i.e., counterfeit, as in 507. On the other hand, if the material does fluoresce at the correct wavelength, it may be determined that the product is authentic, as in 506.

Alternatively, in operation 502, it may be determined if the material fluoresces at a first predetermined emission wavelength and if the material fluoresces at a first predetermined intensity. If the material does not fluoresce at the correct wavelength and intensity, then it may be determined that the product is not authentic, as in 507. On the other hand, if the material does fluoresce at the correct emission wavelength and intensity, it may be determined that the product is authentic, as in 506.

The operation 502 may only include checking fluorescence at a first predetermined emission wavelength. Optionally, however, the operation 502 may include checking fluorescence at two or more predetermined emission wavelengths. In this embodiment, the test may be repeated until all wavelengths have been tested, as in 503. For example, the operation 502 may include checking fluorescence at first and second predetermined emission wavelengths. If the material fluoresces at the first and second predetermined emission wavelengths, it may be determined that the product is authentic, as in 506. On the other hand, if the material does not fluoresce at both emission wavelengths, then it may be determined that the product is not authentic, as in 507. In one embodiment, a method for determining whether a product is authentic may terminate with operation 503. Alternatively, one or more additional tests may be performed.

In one embodiment an additional test is performed in operation 504. In operation 504, the nanoscale structure of the silica particles may be examined using electron microscopy or an similar technique. Operation 504 may include inspecting the size or shape or other structural characteristic of the fluorescent material in a substance and comparing an observation with an expected or "controlled for" size or shape of the fluorescent material. In operation 505, it may be determined if the observed structural characteristic is substantially the same as the expected structural characteristic. If the expected structure is not observed, then it may be determined that the article is not authentic, as in 507. If the expected structure is observed, then it may be determined that the product is genuine, as in 506.

Illustrative Experimental Protocols

The following illustrative experimental protocols are prophetic examples and may be reproduced in a laboratory environment.

1. Preparation of Fluorescent Silica Particles Under Stöber Conditions—TEOS, Two Fluorescent Dyes Dyes are prepared by mixing together solutions A and B. Solution A contains ammonia (2M, 3.75 mL) and water. Solution B contains tetraethyl orthosilicate (TEOS, 0.355 g., 1.7 mmoles), 4,4'-bis((4-triethoxysilyl)styryl)biphenyl (0.01-1.0 mol % of TEOS), and N—N'-bis(3-triethoxysilyl)propyl-perylene-3,4:9,10-tetracarboxdiimide (0.01-1.0 mol % of TEOS) diluted to mL with anhydrous ethanol. Solution A is added quickly to solution B and mixed using a stir bar for approximately 24 hours at room temperature, with the total volume at 10 mL. Particle formation begins within a few minutes.

2. Preparation of Fluorescent Silica Particles Under Microemulsion Conditions—TEOS, One Fluorescent Dye, 200 nm MCM-41-Type Mesoporous Silica Nanoparticles Particles are prepared through a modified Lai et al. synthesis using n-cetyltrimethylammonium bromide (CTAB), sodium hydroxide, deionized water, and tetraethyl orthosilicate (TEOS). All chemicals used are as purchased. CTAB (1.00 g., $2.74 \times 10^{-3}$ mol) is dissolved in deionized water (480 mL) in a 1000 mL round bottom with a condenser. NaOH (2.00 M, 3.50 mL) is then added to the CTAB solution, and the temperature is raised to 80° C. using an oil bath. TEOS (6.2 mL, $2.78 \times 10^{-2}$ mol) and the bridged silane fluorescent dye (0.01-1.0 mol % of TEOS) are then added to the surfactant solution. The mixture is stirred (440 rpm) for 2 hr to give rise to white precipitates.

The solid product is filtered, washed with deionized water and methanol, and dried in air. To remove the surfactant template (CTAB), 1.50 g. of synthesized nanoparticles are refluxed for 24 hr in a solution of HCl (9.00 mL, 37.4%) and methanol (160 mL), followed by extensive washes with deionized water and methanol. The resulting surfactant-removed silica nanoparticles are dried in vacuo to remove remaining solvent in the mesopores.

3. Surface Modification of Fluorescent Silica Particles—Polyethylene Glycol, MCM-41-Type Mesoporous Silica Nanoparticles Particles are prepared as described above. Dried particles are dispersed in a solution of methoxy-polyethylene glycol-silane (3 mM) in THF or toluene. Particles are stirred for 4 hr at 60° C. The solution is then filtered and extensively washed with toluene and ethanol, and dried in vacuo.

What is claimed is:

1. A fluorescent material, comprising:
   a silica matrix;
   first fluorescent dye compounds covalently bonded to the silica matrix, the first fluorescent dye compounds having a first emission wavelength; and
   second fluorescent dye compounds covalently bonded to the silica matrix, the second fluorescent dye compounds having a second emission wavelength,
   wherein the first and second emission wavelengths are different wavelengths.

2. The material of claim 1, further comprising a dispersive functional group attached to a surface of the fluorescent material.

3. The material of claim 1, wherein the fluorescent material is monodisperse.

4. The material of claim 1, wherein the first fluorescent dye compounds have an emission wavelength at or above the visible spectrum.

5. A method for producing a fluorescent material, comprising:
   combining silane monomers and fluorescent silane dyes; and initiating a polymerization reaction between the silane monomers and the fluorescent silane dyes, thereby creating fluorescent dye compounds covalently bonded to a silica matrix, wherein the fluorescent silane dyes comprise first fluorescent silane dyes and second fluorescent silane dyes, the first fluorescent silane dyes and second fluorescent silane dyes having different emission wavelengths.

6. The method of claim 5, wherein the fluorescent silane dyes are bridged fluorescent silane dyes.

7. The method of claim 5, further comprising modifying a surface of the fluorescent material with a dispersive functional group.

8. The method of claim 5, further comprising performing a Stöber process.

9. The method of claim 5, further comprising performing a microemulsion process.

10. The method of claim 5, wherein the fluorescent silane dyes fluoresce at a wavelength at or above the visible spectrum.

11. A method for verifying authenticity of a product, comprising:

exposing a fluorescent material to incident radiation, the fluorescent material comprising a silica matrix and first and second fluorescent dye compounds covalently bonded to the silica matrix, the first fluorescent dye compounds having a first emission wavelength and the second fluorescent dye compounds having a second emission wavelength, wherein the first and second emission wavelengths are different wavelengths; and detecting emissive radiation having the first emission wavelength and the second emission wavelength to verify the authenticity of the product.

12. The method of claim 11, further comprising inspecting the material using electron microscopy to determine presence of a structural characteristic of the fluorescent material to verify the authenticity of the product.

13. The method of claim 11, wherein the fluorescent dye compounds have an emission wavelength at or above the visible spectrum.

14. The method of claim 11, further comprising:

dispersing the fluorescent material in a substance at a predetermined concentration; and detecting if the material fluoresces at a first predetermined intensity to verify the authenticity of the product.

15. A fluorescent material comprising:

a silica matrix, comprising silicon, oxygen, first fluorescent dye compounds, and second fluorescent dye compounds, wherein:

the first fluorescent dye compounds are covalently bonded to at least some silicon atoms in the silica matrix and have a first emission wavelength, the second fluorescent dye compounds are covalently bonded to at least some silicon atoms in the silica matrix and have a second emission wavelength, and the first and second emission wavelengths are different wavelengths.

16. The material of claim 15, further comprising a dispersive functional group attached to the fluorescent material.

17. The material of claim 15, wherein the fluorescent material is monodisperse.

18. The material of claim 15, wherein the fluorescent dye compounds fluoresce at a wavelength at or above the visible spectrum.

* * * * *